(12) United States Patent
Betts

(10) Patent No.: US 10,039,477 B2
(45) Date of Patent: Aug. 7, 2018

(54) LASER-ASSISTED SURGICAL PROCEDURE TO RESTORE SENSOR NEURAL HEARING LOST

(71) Applicant: Juan Betts, Chestnut Hill, MA (US)

(72) Inventor: Juan Betts, Chestnut Hill, MA (US)

(73) Assignee: Juan Betts, Chestnut Hill, MA (US)

( * ) Notice: Subject to any disclaimer, the term of this patent is extended or adjusted under 35 U.S.C. 154(b) by 500 days.

(21) Appl. No.: 14/170,954

(22) Filed: Feb. 3, 2014

(65) Prior Publication Data

US 2014/0221777 A1 Aug. 7, 2014

Related U.S. Application Data

(60) Provisional application No. 61/760,476, filed on Feb. 4, 2013.

(51) Int. Cl.
| | |
|---|---|
| *A61B 5/12* | (2006.01) |
| *A61B 5/00* | (2006.01) |
| *A61B 18/20* | (2006.01) |
| *A61B 34/10* | (2016.01) |
| *A61B 18/00* | (2006.01) |
| *A61B 5/107* | (2006.01) |
| *A61B 17/00* | (2006.01) |

(52) U.S. Cl.
CPC ............ *A61B 5/126* (2013.01); *A61B 5/0082* (2013.01); *A61B 18/20* (2013.01); *A61B 5/1076* (2013.01); *A61B 5/121* (2013.01); *A61B 2017/00787* (2013.01); *A61B 2018/00327* (2013.01); *A61B 2018/00601* (2013.01); *A61B 2034/104* (2016.02)

(58) Field of Classification Search
None
See application file for complete search history.

(56) References Cited

U.S. PATENT DOCUMENTS

| | | | | |
|---|---|---|---|---|
| 5,591,157 | A | * 1/1997 | Hennings | A61B 18/20 606/10 |
| 2006/0282009 | A1 | * 12/2006 | Oberg | A61B 5/0084 600/559 |

OTHER PUBLICATIONS

Dalhoff et al, Distortion product otoacoustic emissions measured as vibration on the eardrum of human subjects, Proc Natl Acad Sci USA, Jan. 30, 2007, 104 (5): 1546-1551.*
Dalhoff et al, Distortion product otoacoustic emissions measured as vibration on the eardrum of human subjects, Proc Natl Acad Sci USA, Jan. 30, 2007 104 (5): 1546-1551).*
Cheng et al, Motion of the surface of the human tympanic membrane measured with stroboscopic holography, Hear Res. May 2010; 263(1-2): 66-77.*

(Continued)

*Primary Examiner* — Lynsey Eiseman
*Assistant Examiner* — Qingjun Kong
(74) *Attorney, Agent, or Firm* — Foley & Lardner LLP

(57) ABSTRACT

The present application is directed towards method and systems for determining appropriate morphology changes of an eardrum to restore sensor neural hearing. The methods include receiving a measurement of an audibility threshold, a map of a surface area of an eardrum of the patient, and an impedance of the eardrum of the patient. The methods further include determining, based on at least one of the audibility threshold, the map of the surface area, and the impedance, a thickness value to modify a morphology of a portion of the eardrum of the patient to improve hearing of the patient.

26 Claims, 9 Drawing Sheets

(56) References Cited

OTHER PUBLICATIONS

Maheswaran, Sound, Lecture for Phy1222, Spring 2003, College of Engineering, Northeastern University.*
Fay et al, The discordant eardrum, Proc Natl Acad Sci USA, Dec. 26, 2006, 103 (52): 19743-8.*

* cited by examiner and the detailed description.

LASER-ASSISTED SURGICAL PROCEDURE TO RESTORE SENSOR NEURAL HEARING LOST

RELATED APPLICATIONS

This patent application claims the benefit of U.S. Provisional Patent Application No. 61/760,476, filed on Feb. 4, 2013, entitled "Laser-Assisted Surgical Procedure to Restore Sensor Neural Hearing Lost," the disclosure of which is incorporated herein by reference.

BACKGROUND

Age related sensorineural hearing lost, also referred to as Presbycusis, naturally occurs as a person ages. Presbycusis is most evident at higher frequencies, for example at frequencies above 4000 Hz. A normal hearing frequency range for an average person spans from 20 Hz to 20 KHz. However, as people age their ability to hear at the higher frequencies, for example above 4000 Hz, is affected. An estimated one third of adults ages 65 to 75 and half of adults over 75 have some degree of hearing loss.

Presently, nearly all age-related sensorineural hearing loss treatments are intrusive and frequently based on an active electro-mechanical medical device. These devices are either placed externally (e.g. hearing aids) or implanted internally (e.g. cochlear implants).

SUMMARY

The foregoing summary is illustrative only and is not intended to be in any way limiting. In addition to the illustrative aspects, embodiments, and features described above, further aspects, embodiments, and features will become apparent by reference to the following drawings and the detailed description.

The present disclosure is directed to methods and systems that restore sensor neural hearing lost without the need of an external or implantable medical device. The hearing loss can be restored by modifying the morphology of the eardrum/ossicles structure. This morphology change causes a structural acoustic behavior change both from an acoustic to structure perspective (acoustic coupling) as well as from a structural vibro-acoustic response.

More particularly, such methods and systems involve entering several inputs into a pre-determined algorithm. The algorithm computes the morphology changes of the eardrum/ossicles structure required to shift the amplitude and frequency of the acoustic energy of the impinging waves on the eardrum and direct this energy to the frequencies of hearing lost. Therefore, amplification in the hearing lost spectrum (typically higher frequencies is achieved passively without the need of a device).

In one aspect, the present disclosure is related to a method for determining appropriate morphology changes of an eardrum to restore sensor neural hearing. The method includes receiving, by a processor executing on a device, a measurement of an audibility threshold, a map of a surface area of an eardrum of the patient, and an impedance of the eardrum of the patient, and determining, by the processor, based on at least one of the audibility threshold, the map of the surface area, and the impedance, a thickness value to modify a morphology of a portion of the eardrum of the patient to improve hearing of the patient. In some embodiments, the measurement of the audibility threshold is received from a hearing test device. In an embodiment, the method includes receiving a minimum perceptible free-field intensity level of a tone that the patient can detect. In some embodiments, the map of the surface area is a three dimensional representation of the surface of the eardrum. In an embodiment, the thickness value corresponds to a thickness of a tympanic membrane of the patient.

The method further includes determining, by the processor, a modification to a shape of the eardrum to change a structural-acoustic response characteristic of the eardrum to improve hearing of the patient. In some embodiments, the method includes determining, by the processor, an impedance value to produce an impedance match between the sound waves transmitted from an auditory canal of the eardrum to an inner ear of the eardrum. The method further includes calculating, by the processor, a maximum power value for frequencies of decreased audibility of the patient. In some embodiments, the thickness value corresponds to a modification to the morphology of the eardrum to increase an acoustic power factor of the eardrum to the maximum power value for frequencies of decreased audibility of the patient. The method further includes calculating, by the processor, a minimum masking factor for frequencies of decreased audibility of the patient. In some embodiments, the thickness value corresponds to a modification to the morphology of the eardrum to decrease a masking factor of the eardrum to the minimum masking value. The method further includes transmitting, by the processor, the thickness value to a laser device. In some embodiments, the processor is executing on a laser device.

In another aspect, the present disclosure is related to a system for determining appropriate morphology changes of an eardrum to restore sensor neural hearing. The system includes a processor. In some embodiments, the processor is configured to receive a measurement of an audibility threshold, a map of a surface area of an eardrum of the patient, and an impedance of the eardrum of the patient, and determine, based on at least one of the audibility threshold, the map of the surface area, and the impedance, a thickness value to modify a morphology of a portion of the eardrum of the patient to improve hearing of the patient. In an embodiment, the processor is configured to receive the audibility threshold from a hearing test device. In some embodiments, the processor is configured to receive a minimum perceptible free-field intensity level of a tone that the patient can detect. In an embodiment, the map of the surface area is a three dimensional representation of the surface of the eardrum. In some embodiments, the thickness value corresponds to a thickness of a tympanic membrane of the patient.

In an embodiment, the processor is further configured to determine a modification to a shape of the eardrum to change a structural-acoustic response characteristic of the eardrum to improve hearing of the patient. In some embodiments, the processor is configured to determine an impedance value to produce an impedance match between the sound waves transmitted from an auditory canal of the eardrum to an inner ear of the eardrum. In an embodiment, the processor is configured to calculate a maximum power value for frequencies of decreased audibility of the patient. In some embodiments, the thickness value corresponds to a modification to the morphology of the eardrum to increase an acoustic power factor of the eardrum to the maximum power value for frequencies of decreased audibility of the patient. In an embodiment, the processor is configured to calculate a minimum masking factor for frequencies of decreased audibility of the patient. In some embodiments, the thickness value corresponds to a modification to the morphology of the eardrum to decrease a masking factor of the eardrum to the minimum masking value. In an embodiment, the processor is configured to transmit the thickness value to a laser device. In some embodiments, the processor is executing on a laser device.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are; therefore, not to be considered limiting of its scope, the disclosure will be described with additional specificity and detail through use of the accompanying drawings.

DETAILED DESCRIPTION

Figure 1A:
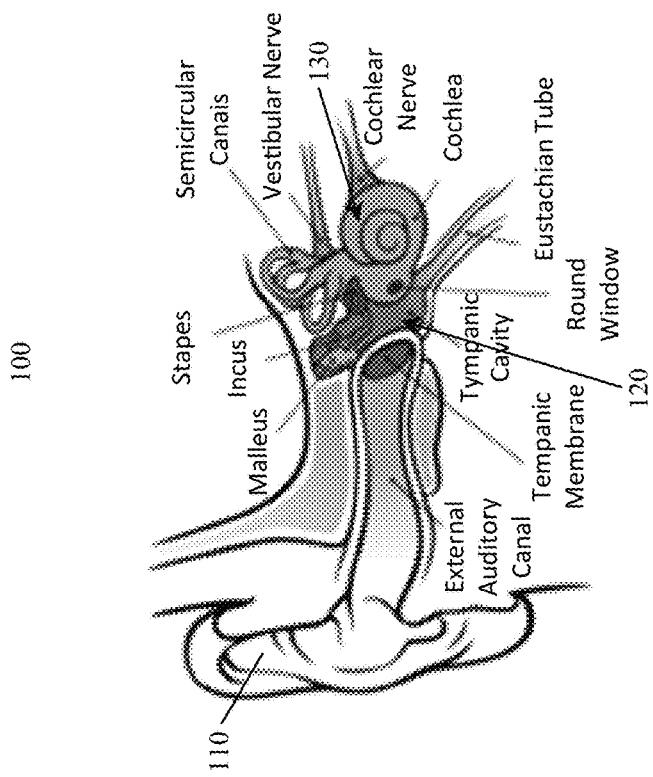
FIG. 1A depicts an anatomy of a human ear.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein are methods and systems for restoring sensor neural hearing loss of a patient by modifying the morphology of the eardrum/ossicles structure of the patient's ear. By modifying the morphology of the patient's ear, the structural acoustic response of the ear is also modified, resulting in improved hearing at frequencies of decreased audibility for the patient. Thus, hearing loss is restored without the need of external or implantable hearing aid devices.

Hearing aids typically require a patient to wear externally or implanted hearing devices to achieve hearing restoration. The present application eliminates the need for a patient to wear a device to achieve hearing restoration.

Figure 1B:
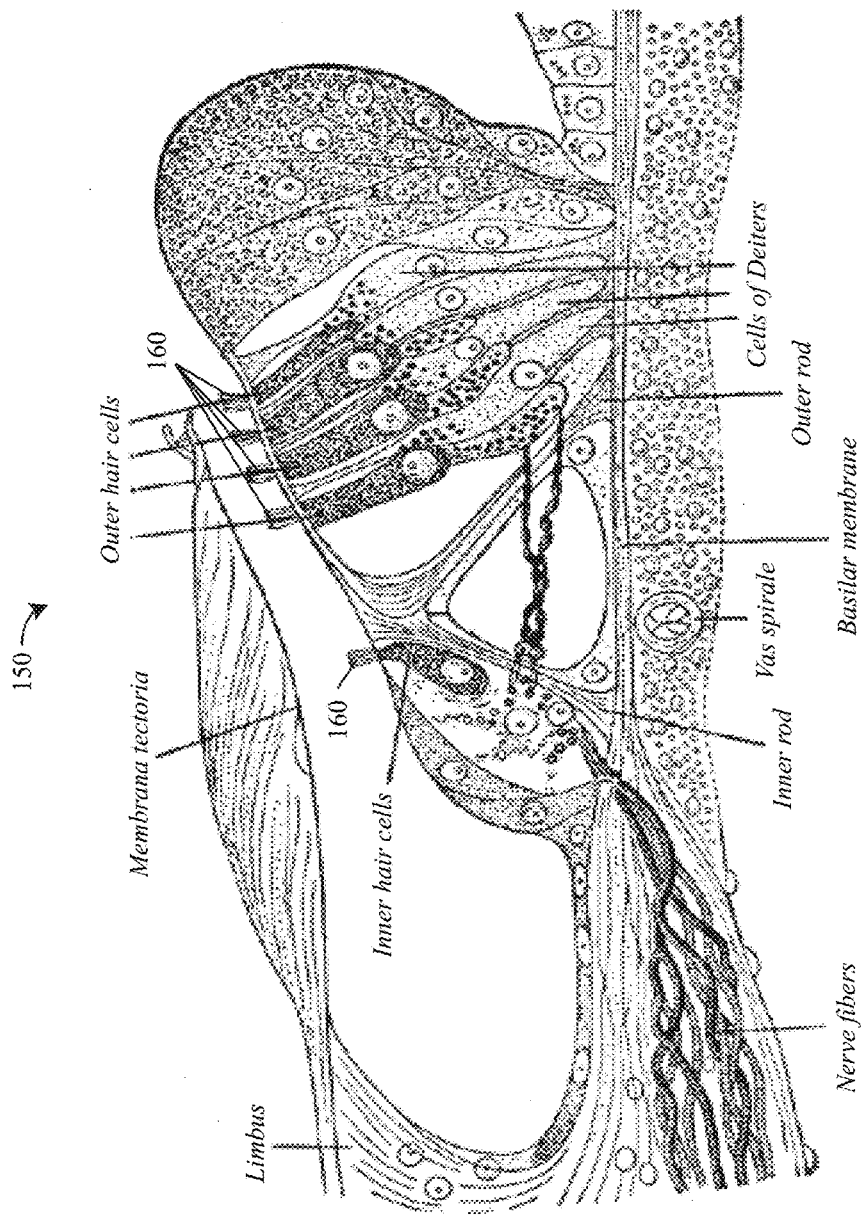
FIG. 1B depicts an expanded view of portions of an inner ear.

FIGS. 1A and 1B illustrate the anatomy of a human ear and an inner ear section of the human ear, respectively. As illustrated in FIG. 1A, the human ear 100 is composed of three sections an outer ear 110, a middle ear 120, and an inner ear 130. The outer ear 110 generally includes the pinna (the outer horn) and the auditory canal. The middle ear 120 generally includes the eardrum (i.e., tympanic membrane), an air filled cavity behind the eardrum (i.e., tympanic membrane) and three ossicles: the malleus, the incus, and the stapes. The inner ear 130 includes the vestibule, the semicircular canals, and the cochlea. As acoustic waves hit the human ear 100, the acoustic waves enter through the auditory canal and hit the eardrum (tympanic membrane). The eardrum converts the acoustic energy in the air into mechanical vibration that get transmitted through the ossicles of the middle ear 120 and into the fluid-filled inner ear 130.

In particular, FIG. 1B depicts an expanded view of a cochlea 150 of an inner ear in accordance with an illustrative embodiment. The cochlea 150 of the inner ear includes hair like cells referred to as stereocilia 160. The stereocilia 160 responds to the fluid motion and convert this mechanical excitation into electrical stimulus that travels through the cochlear nerve and into the brain, which is then interpreted as hearing.

As a person ages, the stereocilia 160 degenerates, resulting in the stereocilia losing their electro-mechanical properties and thus resulting in hearing loss. This age related sensorineural hearing lost, also referred to as Presbycusis, naturally occurs as a person ages. Presbycusis is most evident at higher frequencies, for example at frequencies above 4000 Hz. A normal hearing frequency range for an average person spans from 20 Hz to 20 KHz. However, as people age their ability to hear at the higher frequencies, for example above 4000 Hz, is affected. An estimated one third of adults ages 65 to 75 and half of adults over 75 have some degree of hearing loss.

Presently, nearly all age-related sensorineural hearing loss treatments are intrusive and frequently based on an active electro-mechanical medical device. These devices are either placed externally (e.g. hearing aids) or implanted internally (e.g. cochlear implants). These devices basically amplify the incoming sound waves and reduce masking (the amount the threshold of audibility of the signal is raised in the presence of noise).

Accordingly, this disclosure is generally related to methods and systems to partly restore age-related sensorineural hearing lost, without the need of invasive surgery to implant a medical device (e.g. cochlear implants) or having to wear an external placed hearing aid.

The methods and systems described herein restore hearing without the need of invasive surgery to implant a medical device or having to wear an external placed hearing aid. In particular, this disclosure is generally related to a method to guide a laser in performing cuts on the eardrum (i.e., tympanic membrane) to change the morphology of the eardrum. In some embodiments, the laser cuts may modify the acoustic impedance characteristics of the eardrum with respect to the incident acoustic wave coming from the auditory canal. In an embodiment, the impedance changes affect the amplitudes and frequencies of acoustic energy that gets transmitted from the tympanic membrane, through the ossicles structure (malleus, incus, and stapes), and ultimately into the cochlea.

Figure 2B:
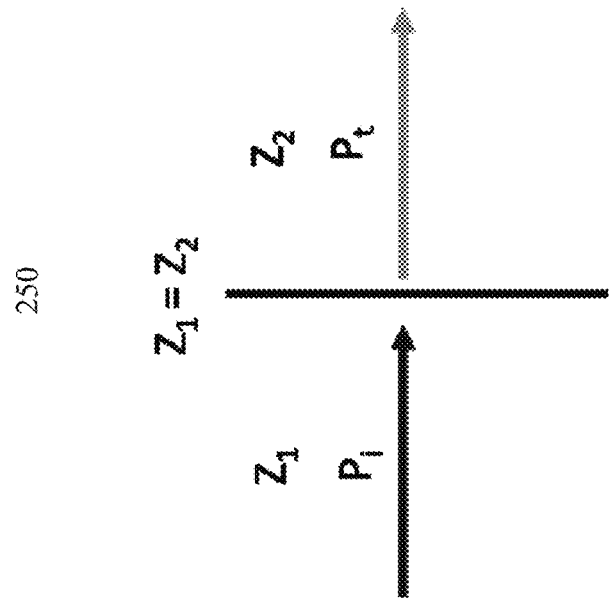
FIG. 2B is a second graph illustrating incidence acoustic transmission through a medium discontinuity.
Figure 2A:
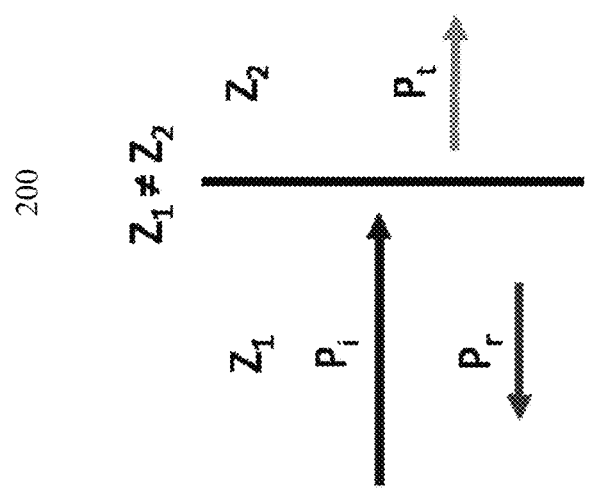
FIG. 2A is a first graph illustrating incidence acoustic transmission through a medium discontinuity.

FIGS. 2A and 2B illustrate the relationship between acoustic pressure traveling from the auditory canal of the outer ear, through the tympanic membrane, to the inner ear. As illustrated in the graph 200 of FIG. 2A, when an acoustic pressure (Pi) travelling through a medium hits a discontinuity, in this case the tympanic membrane, part of the wave is transmitted (Pt) through to the inner ear and part of the wave is reflected (Pr). The amount of reflection depends on a variable called acoustic impedance (Z) between the two mediums. In some embodiments, the acoustic impedance (Z) at any point may be defined as (Z=P/v), where P is the instantaneous acoustic pressure and v is a particle velocity. For plane acoustic waves, the acoustic impedance (Z) is a constant for a given medium and defined as (Z=ρc), where ρ is the density of the medium and c is the acoustic propagation speed. As the acoustic impedance (z) of the two medias equalize (i.e., Z1=Z2), more of the incident wave gets transmitted, as illustrated in the graph 250 of FIG. 2B The tympanic membrane and ossicles, with its associated ligaments and muscles, act as an impedance match, although not perfect, between the air in auditory canal and the fluid in the inner ear thereby maximizing the amount of the acoustic energy being transmitted.

The surface eardrum impedance Ze(f, Ω, τ) is itself a function of the frequency (f), the location in the surface of the ear (Ω), and the surface thickness of the portion of the ear (τ). In some embodiments, as will be described in greater detail below, to maximize the amount of acoustic energy being transmitted from the auditory canal of the outer ear to the fluid in the inner ear, a laser cut may be performed to reduce the thickness of the tympanic membrane. In an embodiment, a laser cut algorithm determines the appropriate thickness value to reduce the thickness of the tympanic membrane. In some embodiments, this reduction modifies the surface morphology thickness (τ) of the eardrum using laser cuts thereby changing Ze(f, Ω, τ) as to differentially maximize transmission of acoustic energy at frequencies of hearing lost and reduce the level of masking (the amount the threshold of audibility of the signal is raised in the presence of noise). The process is general composed of four steps, as illustrated in FIG. 3.

Figure 3:
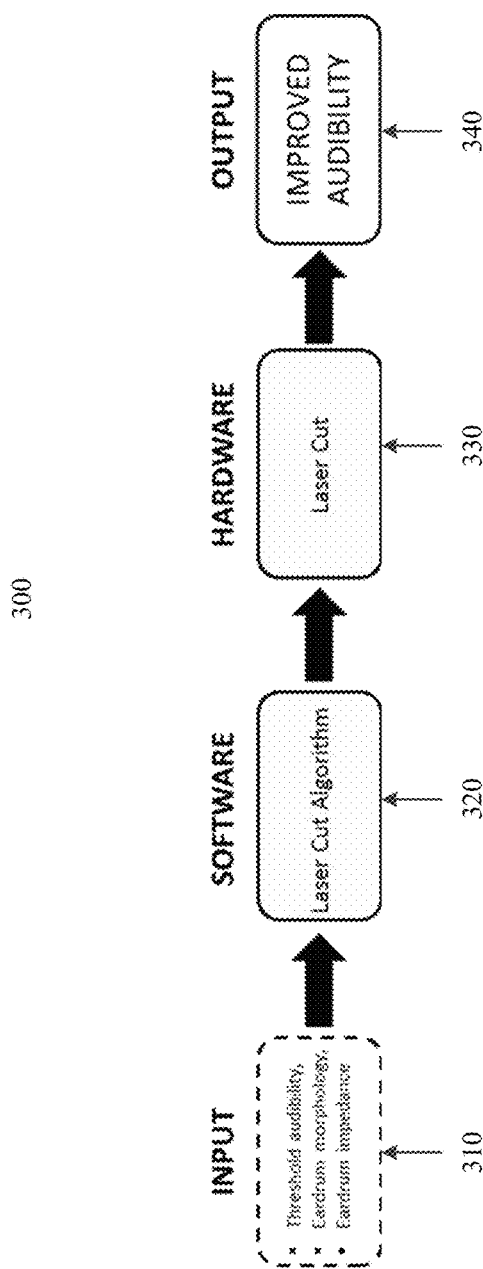
FIG. 3 depicts a flow diagram of a method for a laser assisted procedure to improve hearing in a patient.

FIG. 3 depicts a flow diagram of a method 300 for a laser assisted procedure to improve hearing in accordance with one illustrative embodiment.

The method can apply to a computing device that executes a processor. The method includes receiving, by a processor, a set of input measurements (310). The processor may determine, based on a laser cut algorithm, a thickness value to reduce a morphology of a portion of an eardrum of a patient (320). The processor may transmit this value to a laser cut device (330). The laser cut device may perform cuts to the portion of the eardrum of the patient, responsive to the thickness value received from the processor (340).

Figure 4A:
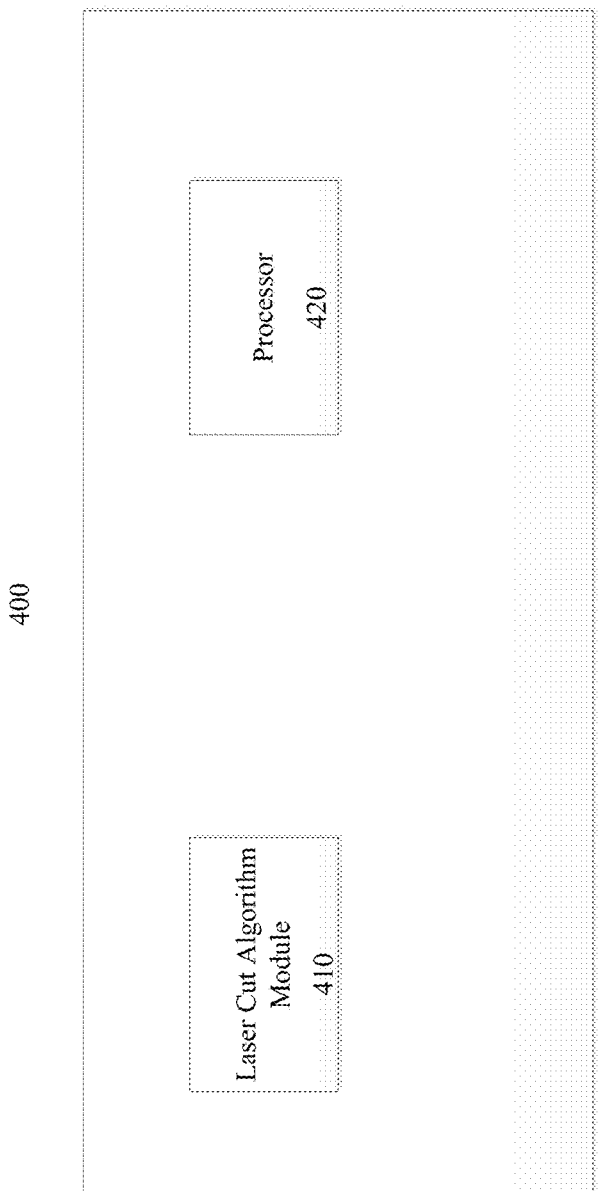
FIG. 4A depicts a block diagram of a system for determining a thickness value to modify the morphology of a portion of the eardrum.

Steps 310 and 320 will be discussed in greater detail with reference to FIGS. 4A and 4B. FIG. 4A depicts a block diagram of a system 400 for determining a thickness value to modify the morphology of a portion of the eardrum. The system 400 includes a laser cut algorithm module 410 and a processor 420. In some embodiments, the laser cut algorithm module 410 is configured to receive a set of input measurements. In an embodiment, the laser cut algorithm module 410 may receive the set of input measurements from the processor 420. In other embodiments, the laser cut algorithm module 410 may receive the set of input measurements from a computing device. The computing device may include a device for performing a hearing test, a laser device, and/or a device for measuring impedance, for example, a vibrometer. In some embodiments, the laser cut algorithm module 410 is configured to determine a thickness value to reduce a morphology of a portion of an eardrum of a patient. In an embodiment, the laser cut algorithm module 410 is communicatively coupled to the processor 420. In some embodiments, the laser cut algorithm module 410 is configured to transmit output to the processor 420. The output may include a thickness value required to reduce the morphology of the eardrum of the patient to improve the patient's hearing. In some embodiments, the laser cut algorithm module 410 is executing on the same device the processor 420 is executing on.

In some embodiments, the processor 420 is configured to configured to receive a set of input measurements. In some embodiments, the processor 420 may receive the set of input measurements from a computing device. The computing device may include a device for performing a hearing test, a laser device, and/or a device for measuring impedance, for example, a vibrometer. In some embodiments, processor 420 is configured to transmit the set of input measurements to the laser cut algorithm module 410. In an embodiment, the processor 420 may be a component of the laser cut algorithm module 410. In some embodiments, the processor 420 is configured to receive output from the laser cut algorithm module 410. The output may include a thickness value required to reduce the morphology of the eardrum of the patient to improve the patient's hearing. In some embodiments, the processor 420 is configured to determine a thickness value to reduce a morphology of a portion of an eardrum of a patient.

In some embodiments, the processor 420 is configured to receive the an audibility threshold from a hearing test device. In one embodiment, the processor 420 is configured to receive a minimum perceptible free-field intensity level of a tone that the patient can detect. In some embodiments, the processor 420 is configured to receive a map of the surface area of an eardrum of the patient. In one example, the map can be a three dimensional representation of the surface of the eardrum, such as the eardrum surface morphology map 600 illustrated in FIG. 6.

In some embodiments, the processor 420 is configured to determine a modification to a shape of the eardrum to change a structural-acoustic response characteristic of the eardrum to improve hearing of the patient. In an embodiment, the processor can be configured to determine an impedance value to produce an impedance match between the sound waves transmitted from an auditory canal of the eardrum to an inner ear of the eardrum. The impedance match may reduce reflection of an acoustic wave traveling from the ear, as illustrated in FIG. 2A. In some embodiments, the processor is configured to calculate a maximum power value for frequencies of decreased audibility of the patient. In an embodiment, the determined thickness value may correspond to a modification to the morphology of the eardrum to increase an acoustic power factor of the eardrum to the maximum power value for frequencies of decreased audibility of the patient.

In some embodiments, the processor 420 is configured to calculate a minimum masking factor for frequencies of decreased audibility of the patient. In an embodiment, the determined thickness value corresponds to a modification to the morphology of the eardrum to decrease a masking factor of the eardrum to the minimum masking value. In some embodiments, the processor 420 is configured to transmit the thickness value to a laser device. In other embodiments, the processor 420 is executing on a laser device.

Figure 4B:
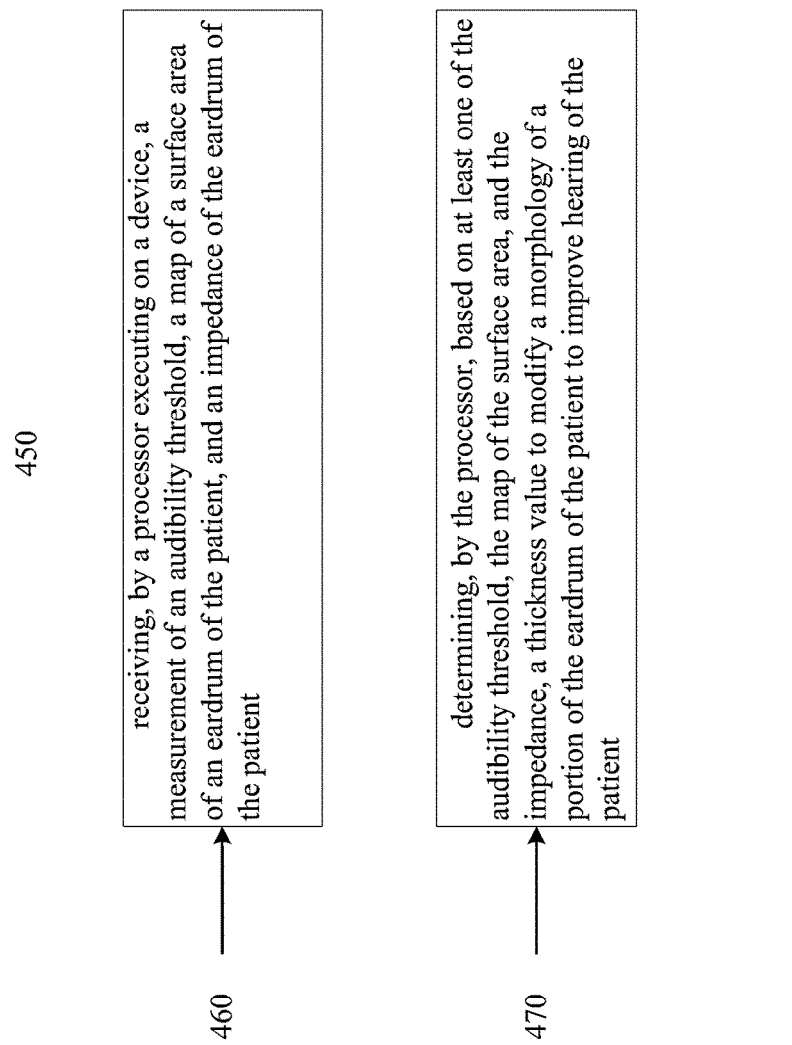
FIG. 4B depicts a flow diagram of an embodiment of a method for determining a thickness value to modify the morphology of a portion of the eardrum.

FIG. 4B depicts a flow diagram of an embodiment of a method for determining a thickness value to modify the morphology of a portion of the eardrum. At step 460, and in more detail, a set of input measurements may be received by a processor executing on a computing device. In some embodiments, the set of input measurements may include at least one of an audibility threshold of a patient, a map of a surface area of an eardrum of the patient, and an impedance of the eardrum of the patient.

Figure 5:
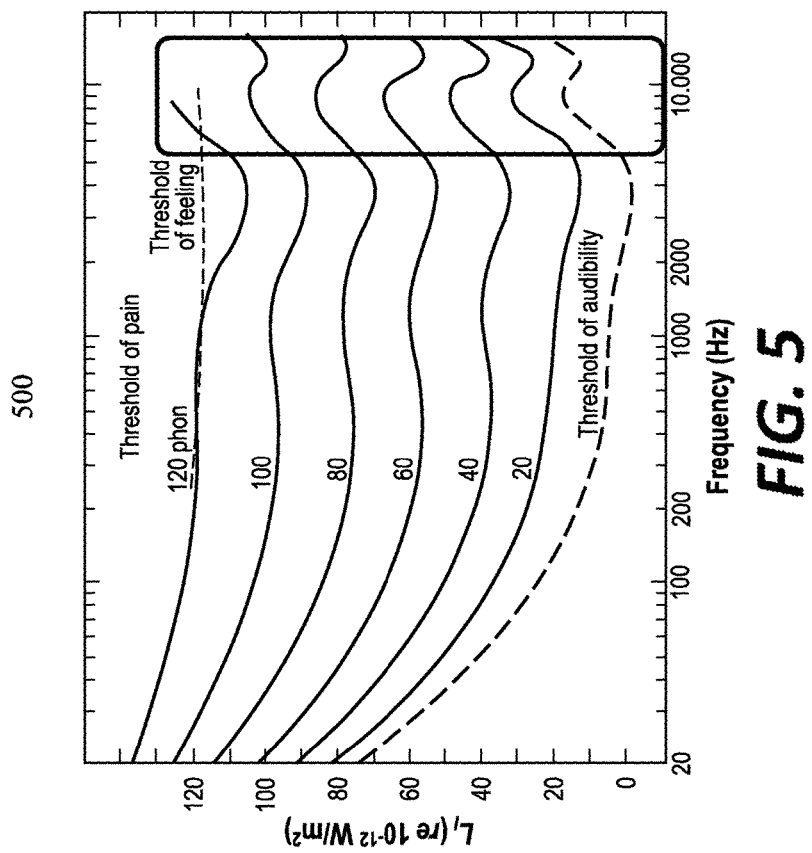
FIG. 5 is a graph of audibility thresholds of a human ear.

In some embodiments, the method may include receiving, by the processor, the audibility threshold of the patient. The audibility threshold of the patient may be determined during a hearing test. In some embodiments, the hearing test may be performed using an audiometer. In other embodiments, the hearing test may be a Weber test or a Rinne test. In some embodiments, the audibility threshold measures a minimum perceptible free-field intensity level of a tone that a patient can detect over the hearing frequency range. FIG. 5 provides one example of a graph 500 illustrating audibility thresholds at various frequencies. As we age, we lose audibility at higher frequencies, for example, above 4000 Hz, which is represented by the boxed region in FIG. 5.

Figure 6:
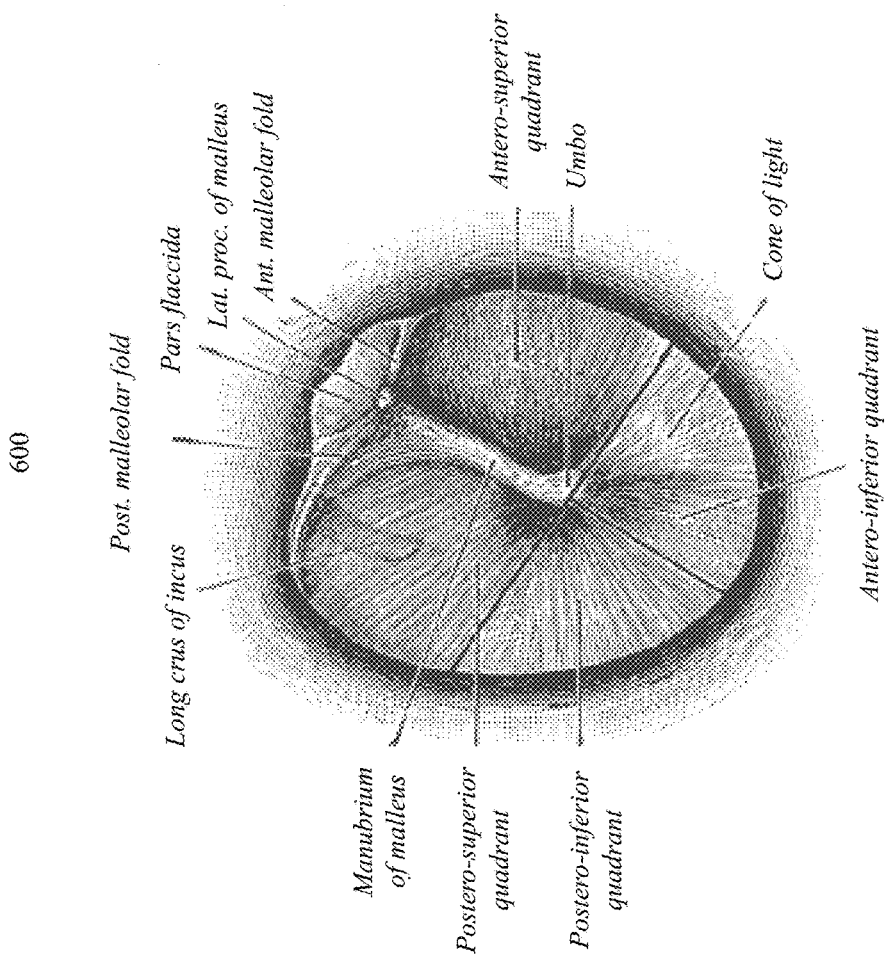
FIG. 6 depicts an eardrum surface morphology map of a human ear.

In some embodiments, the method may include receiving, by the processor, the map of the surface area of the eardrum of the patient. In an embodiment, the map of the surface of the eardrum of the patient may be determined using a laser device. The laser may map the surface morphology of the eardrum resulting in a three dimensional representation of the eardrum surface, as illustrated in FIG. 6. In some embodiments, an average person may have an eardrum that measures around 0.1 mm thick, 8.5 mm in diameter and has a mass of about 14 mg. The eardrum is composed of three layers of tissue: an outer cutaneous layer, a fibrous middle layer and a mucous innermost surface. In some embodiments, by determining an appropriate thickness value for the eardrum, the hearing loss at certain frequencies can be restored.

In some embodiments, the method may include receiving, by the processor, the impedance of the eardrum of the patient. In one embodiments, the impedance of the eardrum can be measured by a microphone array. In some embodiments, the impedance of the eardrum can measured by a Laser Doppler vibrometer. The Laser Doppler vibrometer can measure the vibrational velocity operating shape to a given acoustic excitation. The surface vibration follows the general form of the non-homogeneous wave equation for a thin membrane given by:

$$C_m^2 \nabla^2 y - \frac{d_2 y}{dt^2} = -\frac{P}{P_m} \quad \text{(Equation 1)}$$

Where y is the generalized displacement of the eardrum surface $\Omega$. $\nabla^2$ is the Laplacian operator, t is the time and $\rho_m$ is the surface density (mass per unit area) of the tympanic membrane (the eardrum), P the acoustic pressure and $c_m$ is the wave speed at eardrum. This equation describes a nonlinear system where $\rho_m$, $c_m$, and P are a function of surface thickness pattern $\tau(\Omega)$. The membrane vibrational displacement response in the frequency domain for a given eardrum thickness pattern $\tau(\Omega)$ is given by its modal expansion:

$$y(f,\Omega) = \Sigma_{i=1}^{\infty} A_i(f) \Phi_i(\Omega) \quad \text{(Equation 2)}$$

Where $A_i(f)$ is the modal amplitude, $\phi_i(\Omega)$ is the mode shape. The surface velocity (v=y') is the first derivative in time of the vibrational displacement. Therefore the acoustic surface impedance of the eardrum due to its mechanical properties for a given thickness pattern $\tau(\Omega)$ is given by:

$$Z_e(f, \Omega) = \frac{P}{y'} \quad \text{(Equation 3)}$$

In some embodiments, once the characteristics of a patient's ear have been measured, they can be entered into an algorithm to determine an appropriate thickness value to reduce the thickness of the patient's eardrum. In an embodiment, the algorithm may be a laser cut algorithm.

Still referring to FIG. 4B, at step 470 and in more detail, the processor may determine, based on a laser cut algorithm, a thickness value to reduce a morphology of a portion of an eardrum of a patient. In some embodiments, at least one of the set of input measurements described above with respect to step 310, may be entered into the laser cut algorithm. In an embodiment, the laser cut algorithm may determine a thickness value to reduce the morphology of a portion of the eardrum of a patient based on at least one of the set of input measurements.

In some embodiments, the laser cut algorithm is a multi-objective optimization problem. First, in an embodiment, the laser cut algorithm may be used to determine a thickness value to modify the morphology of the eardrum surface $\tau(\Omega)$ such that the reduction maximizes the transmitted acoustic power ($P_w$) at frequencies of decreased audibility of the patient. Second, in an embodiment, the laser cut algorithm may be used to determine a thickness value to modify the morphology of the eardrum surface $\tau(\Omega)$ such that the reduction minimizes a masking effect caused by the presence of noise at frequencies of decreased audibility of the patient.

In some embodiments, the processor may determine a maximum acoustic power for frequencies of decreased audibility of a patient. The transmitted acoustic power Pw at a given frequency through the eardrum is given by:

$$P_w(f,\tau(\Omega)) = \int_\Omega PP^* M_e^* d\Omega \quad \text{(Equation 4)}$$

Where, * denotes complex conjugate, $M_e$ is the eardrum surface Mobility function of the eardrum. $M_e$ is the inverse of the eardrum impedance $Z_e$ and is given by:

$$M_e = \frac{1}{Z_e} \quad \text{(Equation 5)}$$

Where $Z_e$ is the acoustic impedance due to the surface pattern $\tau(\Omega)$. Additionally, $P_w$ is a function of $\tau(\Omega)$. Thus, the maximum acoustic power may be given by:

$$\text{Max } P_w(f,\tau(\Omega)) \text{ subject to } 0 \leq \tau(\Omega) \leq \tau_{max} \quad \text{(Equation 6)}$$

In some embodiments, the audibility threshold to the laser cut algorithm provides the frequencies (f) to maximize the acoustic power $P_w$. Further, in an embodiment, the measurements obtained from the map of the surface area of the eardrum, as well as the impedance of the eardrum can be used to relate $M_e$ to $\tau(\Omega)$.

Figures 7A, 7B:
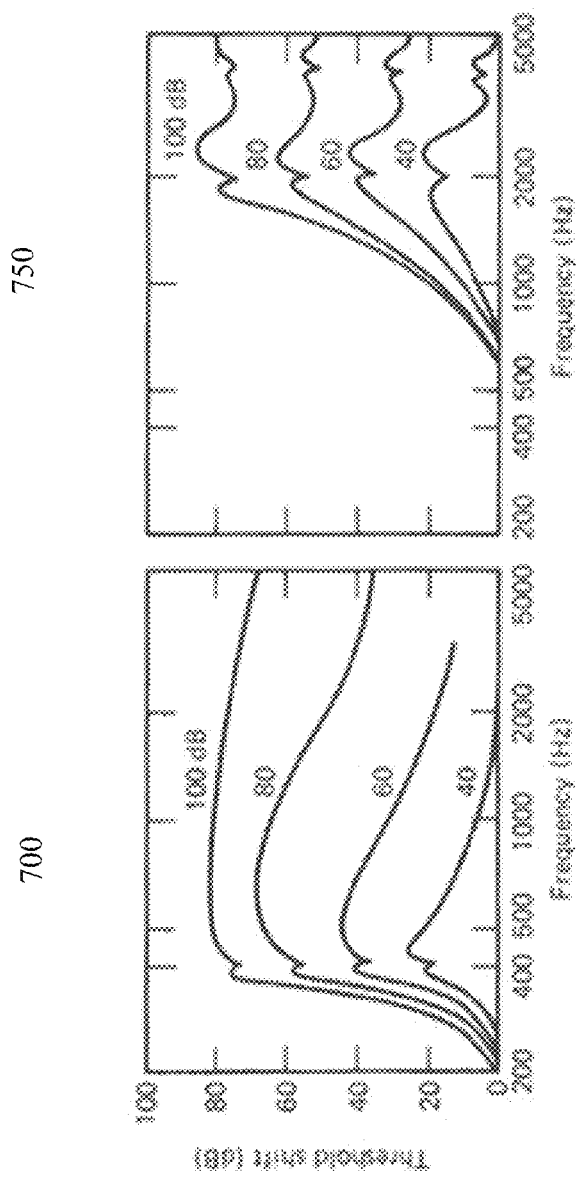
FIG. 7A depicts a first graph illustrating an effect of masking on one pure tone.
FIG. 7B depicts a second graph illustrating an effect of masking on one pure tone.

In some embodiments, the processor may determine a minimum masking value for frequencies of decreased audibility of a patient. In an embodiment, masking is the amount the audibility threshold is reduced by the presence of noise. For example, during a rock concert, the effect of background noise can inhibit the ability to hear and/or understand speakers around you. Generally, masking is expressed as upward shifts in threshold intensity $L_t$ in the presence of noise, as illustrated in FIGS. 7A and 7B. FIG. 7A depicts a graph 700 illustrating masking on one pure tone at 400 Hz. In FIG. 7A, the threshold shift is measured compared to frequency. At around 400 Hz, there is an upward shift in threshold intensity due to the presence of noise. Similarly, FIG. 7B depicts a graph 750 illustrating masking on one pure tone at 2000 Hz. In FIG. 7B, the threshold shift is measured compared to frequency. At around 2000 Hz, there is an upward shift in threshold intensity due to the presence of noise.

Referring back to FIG. 4B and step 470, the laser cut algorithm can determine an appropriate thickness value to reduce the threshold of auditability at selected frequencies below the 4000 Hz by changing surface morphology $\tau(\Omega)$ as to minimize $M_t$ for these frequencies.

Now referring back to FIG. 3, at step 330, the processor may transmit this value to a laser cut device (330). In an embodiment, the laser cut device may be communicatively coupled to the processor. In some embodiments, the processor may be a component of the laser device and executing on the laser device.

At step 340, the laser cut device may perform cuts to the portion of the eardrum of the patient, responsive to the thickness value received from the processor (340). In some embodiments, the inputs to the laser cut algorithm guides the laser cuts that in turn modify the eardrum surface thickness $\tau$. The modification to the morphology of the eardrum (i.e., tympanic membrane) changes the structural acoustic response of the ear. In some embodiments, the modifications shift the amplitude and frequency of the acoustic energy of the impinging waves on the eardrum and direct this energy to the frequencies of hearing loss.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method comprising:
   receiving, by a laser cut algorithm module executing on a processor of a device, as inputs: a measurement of an audibility threshold, a map of a surface area of an eardrum of the patient, and an impedance of the eardrum of the patient;
   providing the audibility threshold to a laser cut algorithm of the laser cut algorithm module to maximize acoustic power;
   providing measurements obtained from the map of the surface area and the impedance of the eardrum to the laser cut algorithm to relate an inverse of an eardrum impedance to a surface thickness pattern;
   determining, by the laser cut algorithm of the laser cut algorithm module, based on at least the inputs of the audibility threshold, the map of the surface area, and the impedance, a thickness value to be provided to a laser device to modify a morphology of a portion of the eardrum of the patient to improve hearing of the patient by changing the eardrum impedance as to differentially maximize transmission of acoustic energy at frequencies of hearing lost and reduce an amount of intensity level that the audibility threshold is raised in a presence of noise; and
   modifying, by the laser device based at least on the laser cut algorithm, the morphology of the portion of the eardrum using the thickness value.

2. The method of claim 1, wherein the measurement of the audibility threshold is received from a hearing test device.

3. The method of claim 1, further comprising computing, by the laser cut algorithm, changes to the morphology to shift an amplitude and frequency of acoustic energy of impinging waves on the eardrum and direct this energy to the frequencies of hearing lost.

4. The method of claim 1, wherein the map of the surface area is a three dimensional representation of the surface of the eardrum.

5. The method of claim 1, wherein the thickness value corresponds to a thickness of a tympanic membrane of the patient.

6. The method of claim 1, further comprising determining, by the laser cut algorithm module, a modification to a shape of the eardrum to change a structural-acoustic response characteristic of the eardrum to improve hearing of the patient.

7. The method of claim 1, further comprising determining, by the laser cut algorithm module, an impedance value to produce an impedance match between the sound waves transmitted from an auditory canal of the eardrum to an inner ear of the eardrum.

8. The method of claim 1, further comprising calculating, by the laser cut algorithm module, a maximum acoustic power value for frequencies of decreased audibility of the patient.

9. The method of claim 8, wherein the thickness value corresponds to a modification to the morphology of the eardrum to increase an acoustic power factor of the eardrum to the maximum acoustic power value for frequencies of decreased audibility of the patient.

10. The method of claim 1, further comprising calculating, by the laser cut algorithm module, a minimum masking factor for frequencies of decreased audibility of the patient.

11. The method of claim 10, wherein the thickness value corresponds to a modification to the morphology of the eardrum to decrease a masking factor of the eardrum to the minimum masking value.

12. The method of claim 1, further comprising transmitting, by the processor, the thickness value to a laser device to perform cuts to the portion of the eardrum of the patient based on the thickness value.

13. The method of claim 1, wherein the processor is executing on a laser device.

14. A system comprising:
a laser device;
a laser cut algorithm module executable on a processor and configured to:
receive as inputs: a measurement of an audibility threshold, a map of a surface area of an eardrum of the patient, and an impedance of the eardrum of the patient,
provide the audibility threshold to a laser cut algorithm of the laser cut algorithm module to maximize acoustic power;
provide measurements obtained from the map of the surface area and the impedance of the eardrum to the laser cut algorithm to relate an inverse of an eardrum impedance to a surface thickness pattern; and
determine, by the laser cut algorithm based on at least the inputs the audibility threshold, the map of the surface area, and the impedance, a thickness value to be provided to the laser device to modify a morphology of a portion of the eardrum of the patient to improve hearing of the patient by changing the eardrum impedance as to differentially maximize transmission of acoustic energy at frequencies of hearing lost and reduce an amount of intensity level that the audibility threshold is raised in a presence of noise,
wherein the laser device is configured to modify, based at least on the laser cut algorithm, the morphology of the portion of the eardrum using the thickness value.

15. The system of claim 14, wherein the laser cut algorithm module is configured to receive the audibility threshold from a hearing test device.

16. The system of claim 14, wherein the laser cut algorithm is further configured to compute changes to the morphology to shift an amplitude and frequency of acoustic energy of impinging waves on the eardrum and direct this energy to the frequencies of hearing lost.

17. The system of claim 14, wherein the map of the surface area is a three dimensional representation of the surface of the eardrum.

18. The system of claim 14, wherein the thickness value corresponds to a thickness of a tympanic membrane of the patient.

19. The system of claim 14, wherein the laser cut algorithm module is configured to determine a modification to a shape of the eardrum to change a structural-acoustic response characteristic of the eardrum to improve hearing of the patient.

20. The system of claim 14, wherein the laser cut algorithm module is configured to determine an impedance value to produce an impedance match between the sound waves transmitted from an auditory canal of the eardrum to an inner ear of the eardrum.

21. The system of claim 14, wherein the laser cut algorithm module is configured to calculate a acoustic maximum power value for frequencies of decreased audibility of the patient.

22. The system of claim 21, wherein the thickness value corresponds to a modification to the morphology of the eardrum to increase an acoustic power factor of the eardrum to the maximum acoustic power value for frequencies of decreased audibility of the patient.

23. The system of claim 14, wherein the laser cut algorithm module is configured to calculate a minimum masking factor for frequencies of decreased audibility of the patient.

24. The system of claim 23, wherein the thickness value corresponds to a modification to the morphology of the eardrum to decrease a masking factor of the eardrum to the minimum masking value.

25. The system of claim 14, wherein the laser cut algorithm module is configured to transmit the thickness value to a laser device.

26. The system of claim 14, wherein the processor is executing on a laser device.

* * * * *